US007026300B2

(12) United States Patent
Brunham et al.

(10) Patent No.: US 7,026,300 B2
(45) Date of Patent: Apr. 11, 2006

(54) **ONE STEP IMMUNIZATION PROCEDURE FOR INDUCING A *CHLAMYDIA* SPECIFIC IMMUNE RESPONSE**

(75) Inventors: Robert C. Brunham, Vancouver (CA); Andrew D. Murdin, Newmarket (CA)

(73) Assignee: Sanofi Pasteur Limited, Toronto ( * ) Notice: Subject to any disclaimer, the term of this patent is extended or adjusted under 35 U.S.C. 154(b) by 14 days.

(21) Appl. No.: 10/699,882

(22) Filed: Nov. 4, 2003

(65) Prior Publication Data

US 2004/0126382 A1 Jul. 1, 2004

Related U.S. Application Data

(62) Division of application No. 09/453,289, filed on Dec. 3, 1999, now Pat. No. 6,676,949.

(60) Provisional application No. 60/110,855, filed on Dec. 4, 1998.

(51) Int. Cl.
*A61K 48/00* (2006.01)

(52) U.S. Cl. .............. 514/44; 424/184.1; 424/234.1; 435/252.3; 435/471; 536/23.1; 536/23.4; 536/23.7; 530/350

(58) Field of Classification Search .......... 435/6, 435/320.1, 456, 252.3, 252.33, 69.3, 71.1, 435/471; 536/23.1, 23.7, 23.4; 514/44; 424/93.2, 190.1, 191.1, 93.1, 93.4, 93.21, 424/184.1, 234.1; 530/350, 389.1, 412

See application file for complete search history.

(56) References Cited

U.S. PATENT DOCUMENTS

| 5,389,368 A | * | 2/1995 | Gurtiss, III .............. 424/200.1 |
| 5,770,714 A | | 6/1998 | Agabian et al. ........... 536/23.1 |
| 6,676,949 B1 | * | 1/2004 | Brunham et al. ........ 424/263.1 |
| 6,696,421 B1 | * | 2/2004 | Brunham .................... 514/44 |

FOREIGN PATENT DOCUMENTS

| EP | 0192033 | | 8/1986 |
| WO | 98/02546 | * | 1/1998 |
| WO | WO 98/02546 | | 1/1998 |
| WO | WO 98/10789 | | 3/1998 |
| WO | WO 98/48026 | | 10/1998 |

OTHER PUBLICATIONS

Grayston, J.T. and S.-P. Wang. 1975. New knowledge of chlamydiae and the diseases they cause. J. Infect. Dis., 132: 87-104.

Grayston, J.T., S.-P. Wang, L.-J. Yeh, and C.-C. Kuo. 1985. Importance of reinfection in the pathogenesis of trachoma. Rev. Infect. Dis. 7:717-725.

Taylor, H.R., et al., 1982. Animal Model of Trachema. II. The importance of repeated infection. Invest. Opthalmol. Visual. Sci. 23:507-515.

(Continued)

*Primary Examiner*—Lynette R. F. Smith
*Assistant Examiner*—Ginny Allen Portner
(74) *Attorney, Agent, or Firm*—Sim & McBurney

(57) ABSTRACT

A host is immunized against infection by a strain of *Chlamydia* by initial administration of an attenuated bacteria harbouring a nucleic acid encoding a *Chlamydia* protein followed by administration of a *Chlamydia* protein in ISCOMs. This procedure enables a high level of protection to be achieved.

11 Claims, 5 Drawing Sheets

OTHER PUBLICATIONS

Taylor, H.R., et al. 1981. An Animal Model for Cicatrizing Trachoma. Invest. Opthalmol. Sci. 21:422-433.

Caldwell, H.D., et al. 1987. Tear and serum antibody response to *Chlamydia trachomatis* antigens during acute chlamydial conjunctivitis in monkeys as determined by immunoblotting. Infect. Immun. 55:93-98.

Wang, S.-P., et al., 1985. Immunotyping of *Chlamydia trachomatis* with monoclonal antibodies. J. Infect. Dis. 152:791-800.

Nichols, R.L., et al., 1973. Immunity to chlamydial infections of the eye. VI. Homologous neutralization of trachoma infectivity for the owl monkey conjunctivae by eye secretions from humans with trachoma. J. Infect. Dis. 127:429-432.

Orenstein, N.S., et al., 1973. Immunity to chlamydial infections of the eye V. Passive transfer of antitrachoma antibodies to owl monkeys. Infect. Immun. 7:600-603.

Ramsey, KH, et al., (Mar. 1991) Resolution of Chlamydia Genital Infection with Antigen-Specific T-Lymphocyte Lines. Infect. and Immun. 59:925-931.

Magee, DM, et al., (1995). Role of CD8 T Cells in Primary *Chlamydia* Infection. Infect. Immun. Feb. 1995. 63:516-521.

Su, H. and Caldwell, HD., (1995) CD4+ T Cells Play a Significant Role in Adoptive Immunity to *Chlamydia trachomatis* Infection of the Mouse Genital Tract. Infect. Immun. Sep. 1995, 63: 3302-3308.

Beatty, PR., and Stephens RS., (1994) CD8+ T Lymphocyte-Mediated Lysis of *Chlamydia*-Infected L Cells Using an Endogenous Antigen Pathway., Journal of Immun. 1994, 153:4588.

Starnbach, MN., Bevan, MJ. and Lampe, MF. (1994), Protective Cytotoxic T. Lymphocytes are Induced During Murine Infection with *Chlamydia trachomatis*, Journal of Immun. 1994, 153:5183-5189.

Starnbach, MN, Bevan, MJ. And Lampe, MF., (1995), Murine Cytotoxic T. Lymphocytes Induced Following *Chlamydia trachomatis* Intraperitonal or Genital Tract Infection Respond to Cells Infected with Multiple Serovars., Infect. & Immun. Sep. 1995, 63:3527-3530.

Igietseme, JU; (1996), Molecular mechanism of T-cell control of *Chlamydia* in mice: role of nitric oxide in vivo. Immunology 1996, 88:1-5.

Igietseme. JU, (1996), The Molecular mechanism of T-cell control of *Chlamydia* in mice; role of nitric oxide. Immunology 1996, 87:1-8.

Ward, M.E. 1992. Chlamydial vaccines—future trends. J. Infection 25, Supp. 1:11-26.

Caldwell, H.D., et al., (1981). Purification and partial characterization of the major outer membrane protein of *Chlamydia trachomatis*. Infect. Immun. 31:1161-1176.

Bavoil, P., Ohlin, A. and Schachter, J., (1984) Role of Disulfide Bonding in Outer Membrane Structure and Permeability in *Chlamydia trachomatis*. Infect. Immun., 44: 479-485.

Campos, M., et al., (1995) A *Chlamydia* Major Outer Membrane Protein Extract as a Trachoma Vaccine Candidate., Invest. Opthalmol. Vis. Sci. 36:1477-1491.

Zhang Y.-X., et al., (1989). Protective monoclonal antibodies to *Chlamydia trachomatis* serovar- and serogroup-specific major outer membrane protein determinants. Infect. Immun. 57:636-638.

Zhang, Y.-X., et al., 1987. Protective monoclonal antibodies recognise epitopes located on the major outer membrane protein of *Chlamydia trachomatis*. J. Immunol. 138:575-581.

Department of Health and Human Services, (1989) Nucleotide and amino acid sequences of the four variable domains of the major outer membrane proteins of *Chlamydia trachomatis*. Report Nos: PAT-APPL-7-324664. National Technical Information Services, Springfield, VA.

Yuan, Y., et al. (1989) Nucleotide and deduced amino acid sequences for the four variable domains of the major outer membrane proteins of the 15 *Chlamydia trachomatis* serovars. Infect. Immun. 57:1040-1049.

Su, H. and Caldwell, H.D. 1992. Immunogenicity of a chimeric peptide corresponding to T-helper and B-cell epitopes of the *Chlamydia trachomatis* major outer membrane protein. J. Exp. Med. 175:227-235.

Su. H., N.G. Watkins. Y.-X. Zhang and H.D. Caldwell (1990). *Chlamydia trachomatis*-host cell interactions: role of the chlamydial major outer membrane protein as an adhesin. Infect. Immun. 58:1017-1025.

Peeling, R., I.W. McClean and R.C. Brunham. (1984). In vitro neutralization of *Chlamydia trachomatis* with monoclonal antibody to an epitope on the major outer membrane protein. Infect. Immun. 46:484-488.

Lucero, M.E. and C.-C. Kuo. (1985). Neutralization of *Chlamydia trachomatis* cell culture infection by serovar specific monoclonal antibodies. Infect. Immun. 50:595-597.

Baehr. W., et al. (1988) Mapping antigenic domains expressed by *Chlamydia trachomatis* major outer membrane protein genes. Proc. Natl. Acad. Sci. USA, 85:4000-4004.

Stephens, R.S., et al. (1988) High-resolution mapping of serovar-specific and common antigenic determinants of the major outer membrane protein of *Chlamydia trachomatis*. J. Exp. Med. 167:817-831.

Conlan, J.W., I.N. Clarke and M.E. Ward. (1988). Epitope mapping with solid-phase peptides: Identification of type-, subspecies-, species-, and genus-reactive antibody binding domains on the major outer membrane protein of *Chlamydia trachomatis*. Mol. Microbiol. 2:673-679.

Conlan, J.W., et al., (1990). Isolation of recombinant fragments of the major outer membrane protein of *Chlamydia trachomatis*: their potential as subunit vaccines. J. Gen. Microbial. 136: 2013-2020.

Morrison, R.P., D.S. Manning, and H.D. Caldwell. (1992). Immunology of *Chlamydia trachomatis* infections. p. 57-84 In T.C. Quinn (ed) Sexually transmitted diseases. Raven Press Ltd., NY.

Kersten, G.F.A. and Crommelin, D.J.A. (1995). Liposomes and ISCOMs as vaccine formulations. Biochimica et Biophysica Acta 1241 (1995) 117-138.

Morein, B., et al., (1990) The iscom—a modern approach to vaccines seminars in Virology, vol. 1, 1990: pp. 49-55.

Mowat & Reid, 1992. Preparation of Immune Stimulating Complexes (ISCOMs) as Adjuvants. Current Protocols in Immunology 1992. Supplement 4: 2.11.1 to 2.11.12.

M.A. Liu et al. Overview of DNA vaccines. 1995. Ann. N.Y. Acad. Sci. 772:15-20.

W.M. McDonnell and F.K. Askari Molecular medicine. 1996. N.Engl. J. Med. 334:42-45.

J.B. Ulmer et al. Heterologous protection against infjuenza by injection of DNA encoding a viral protein. 1993. Science 259:1745-1749, Mar. 19.

M. Sedegah et al. Protection against malaria by immunization with plasmid DNA encoding circumsporozoite protein. 1994. Proc. Natl. Acad. Sci. U.S.A. 91:9866-9870.

A. Darji et al. Oral somatic transgene vaccination using attenuated S. typhimurium. 1997. Cell 91:765-775.

D.R. Sizemore, Attenuated bacteria as a DNA delivery vehicle for DNA-mediated immunization. 1997. Vaccine 15:804-807.

D. O'Callaghan and A. Charbit. High efficiency transformation of *Salmonella typhimurium* and *Salmonella typhi* by electroporation. 1990. Mol. Gen. Genet. 223:156-158.

R. Brunham et al. *Chlamydia trachomatis* from individuals in a sexually transmitted disease cor group exhibit frequent sequence variation in the major outer membrane protein (omp1) gene. 1994. J. Clin. Invest. 94:458-463.

R.P. Morrison et al. Gene knockout mice extablish a primary protective role for major histocompatibility complex class II-Restricted responses in *Chlamydia trachomatis* genital tract infection. 1995. Infect. Immun. 63:4661-4668.

K.Y. Leung et al., Intracellular replication is essential for the virulence of *Salmonella typhimurium*. 1991, PNAS 88(24): 11470-11474.

L.J. Hayes, et al. *Chlamydia trachomatis* major outer membrane protein epitopes expressed as fusions with LamB in an attenuated aro A strain of *Salmonella typhimurium*; their application as potential immunogens. (1991) pp. 1557-1564

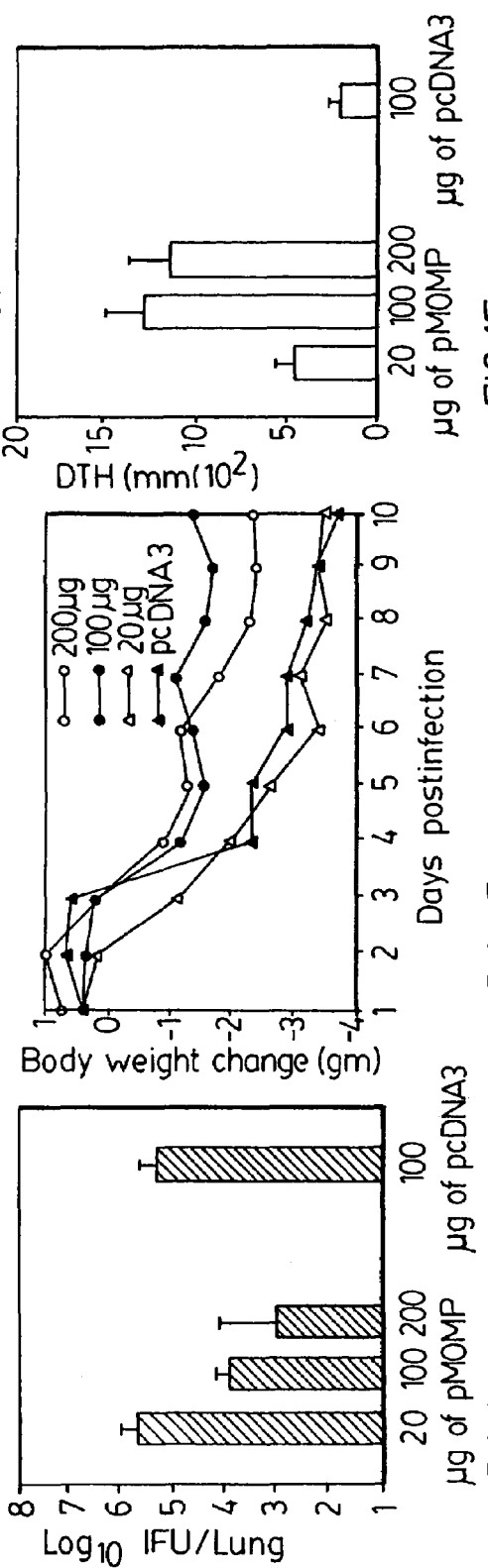

SEQUENCE LISTING

<160> NUMBER OF SEQ ID NOS: 2

<210> SEQ ID NO 1
<211> LENGTH: 35
<212> TYPE: DNA
<213> ORGANISM: Chlamydia trachomatis

<400> SEQUENCE: 1
ggggatccgc caccatgctg cctgtgggga atcct     35

<210> SEQ ID NO 2
<211> LENGTH: 28
<212> TYPE: DNA
<213> ORGANISM: Chlamydia trachomatis

<400> SEQUENCE: 2
ggggctcgag ctattaacgg aactgagc     28

ONE STEP IMMUNIZATION PROCEDURE FOR INDUCING A *CHLAMYDIA* SPECIFIC IMMUNE RESPONSE

REFERENCE TO RELATED APPLICATIONS

This application is a division of U.S. patent application Ser. No. 09/453,289 filed Dec. 3, 1999 (now U.S. Pat. No. 6,676,949), which itself claims priority pursuant to 35 USC 119(e) from U.S. Provisional Patent Application No. 60/110,885 filed Dec. 4, 1998 (now abandoned).

FIELD OF INVENTION

The present invention relates to the field of immunology and, in particular, to a vaccination procedure for protection of a host against disease caused by infection with a bacterium of the *Chlamydiacease* genus, particularly *Chlamydia trachomatis*.

BACKGROUND OF INVENTION

*Chlamydia trachomatis* is a species of the genus *Chlamydiacease*, order Chlamydiales, *C. trachomatis* infects the epithelia of the conjunctivae and the genital tract, causing trachoma and a variety of sexually transmitted diseases (STDs) which can lead to, respectively, blindness or infertility. There are at least 15 serovars of *C. trachomatis*, of which A, B and C are causative agents of trachoma, while serovars D, E. F. G, H, I, J and K are the most common causative agents of the Chlamydial STDs. *C trachomatis* infections are endemic throughout the world. Trachoma is the leading cause of preventable blindness in developing nations, and it is estimated that 600 million people suffer from trachoma worldwide, with as many as 10 million of them being blinded by the disease. In the United States, there are an estimated 3 million cases per year of STDs caused by *C. trachomatis*.

The pathogenesis of trachoma involves repeated ocular infections and the generation of a deleterious hypersensitivity response to chlamydial antigen(s) (refs. 1 to 4—Throughout this specification, various references are referred to in parenthesis to more fully describe the state of the art of which this invention pertains. Full bibliographic information for each citation is found at the end of the specification. The available evidence supports the hypotheses that both secretory IgA and cell-mediated immune responses are important components of protection. Ocular infection in a primate model induces rapid and persistent production of IgA in tears, whereas the presence of IgG in tears is transient, corresponding to the period of peak conjunctival inflammation (refs. 5). Protective immunity following experimental ocular infection in a sub-human primate model is homotypic and resistance to ocular challenge correlates with the presence of serovar-specific antibodies in tears (refs. 1, 2, 6). Tears from infected humans neutralized the infectivity of homologous but not heterologous trachoma serovars for owl monkeys eyes (ref. 7) whereas passive humoral immunization with antitrachoma antibodies was not protective (ref. 8). Several lines of evidence indicate the importance of cell-mediated responses in protection from or clearance of chlamydial infection. B-cell deficient mice can resolve infection, whereas nude mice become persistently infected. Adoptive transfer of at least some chlamydia-specific T-cell lines or clones can cure persistently infected nude mice, and this anti-chlamydial activity is probably a function of the ability of the T-cells to secrete interferon-y (refs. 9 to 16).

Past attempts to develop whole-cell vaccines against trachoma have actually potentiated disease by sensitizing vaccinees (refs. 1, 2). Sensitization has been determined to be elicited to a 57 kD stress response protein (SRP)(HSP60) present in all serovars of *C. trachomatis*. Repeated exposure to the 57 kD SRP can result in a delayed hypersensitivity reaction, causing the chronic inflammation commonly associated with Chlamydial infections. Thus, an immunogenic preparation capable of inducing a strong and enduring mucosal neutralizing. antibody response and a strong cellular immune response without sensitizing the host would be useful (ref. 17).

A most promising candidate antigen for the development of a vaccine is the chlamydial major outer membrane protein (MOMP) (refs. 18 to 20). Other surface proteins and the surface lipopolysaccharide are also immunogenic, but the antibodies they induce have not been found to be protective (refs. 21, 33). The MOMP, which is the predominant surface protein, is an integral membrane protein with a mass of about 40 kDa which, with the exception of four variable domains (VDs) designated I, II, III and IV, is highly conserved amongst serovars. The sequences of all four VDs have been determined for fifteen serovars (refs. 23, 24). Antibodies capable of neutralizing chlamydial infectivity recognize the MOMP (refs. 25, 26, 27, 28). Epitopes to which MOMP-specific neutralizing monoclonal antibodies bind have been mapped for several serovars (refs. 21, 22, 29, 30, 31, 32, 33), and represent important targets for the development of synthetic or subunit vaccines. The binding sites are contiguous sequences of six to eight amino acids located within VDs I or II, and IV, depending on the serovar. Subunit immunogens (e.g. isolated MOMP or synthetic peptides) containing MOMP epitopes can induce antibodies capable of recognizing intact *chlamydiae* (ref. 25). However, conventionally administered subunit immunogens are generally poor inducers of mucosal immunity. It would be useful to formulate chlamydial antigens in such a way as to enhance their immunogenicity and to elicit both humoral and cell-mediated immune responses.

Immune stimulating complexes (ISCOMs) are cage-like structures formed from a mixture of saponins (or saponin derivatives), cholesterol and unsaturated fatty acids. The components of ISCOMs are held together by hydrophobic interactions, and consequently proteins which are naturally hydrophobic (such as MOMP) or which have been treated to expose or add hydrophobic residues can be efficiently incorporated into the ISCOMs as they form (refs. 34, 35, 36).

*C. trachomatis* naturally infects the mucosal surfaces of the eye and genital tract. Local antibody and local cellular immune responses are an important component of protection from mucosal infections. Consequently, it would be useful for a chlamydial vaccine to induce a mucosal immune response including both cellular and antibody components.

DNA immunization is an approach for generating protective immunity against infectious diseases (ref. 37). Unlike protein or peptide based subunit vaccines, DNA immunization provides protective immunity through expression of foreign proteins by host cells, thus allowing the presentation of antigen to the immune system in a manner more analogous to that which occurs during infection with viruses or intracellular pathogens (ref. 38). Although considerable interest has been generated by this technique, successful immunity has been most consistently induced by DNA immunization for viral diseases (ref. 39). Results have been more variable with non-viral pathogens which may reflect differences in the nature of the pathogens, in the immunizing antigens chosen, and in the routes of immunization (ref. 40). Further development of DNA vaccination will depend on elucidating the underlying immunological mechanisms and broadening its application to other infectious diseases for which existing strategies of vaccine development have failed.

The use of attenuated bacteria, in particular *S. typhimurium*, has recently been reported for delivery of plasmid DNA for genetic immunization (refs. 41, 42). This type of delivery offers the added benefit of delivering the DNA to cell types that induce a specific immune response, such as a mucosal immune response. This type of vaccination also offers the advantages of being safe, as many safe, attenuated strains of *Salmonella* are readily available, and cost effective.

EP 0192033 B1 and U.S. Pat. 5,770,714 describe the provision of a DNA construct for the expression, in vitro, of *Chlamydia trachomatis* MOMP polypeptides comprising the following operably linked elements:

a transcriptional promoter, a DNA molecule encoding a *C. trachomatis* MOMP polypeptide comprising a MOMP polynucleotide at least 27 base pairs in length from a sequence provided in Appendix A thereto, and a transcriptional terminator, wherein at least one of the transcriptional regulatory elements is not derived from *Chlamydia trachomatis*.

There is no disclosure or suggestion in this prior art to effect DNA immunization with any such constructs.

Copending U.S. patent application Ser. No. 08/893,381 filed Jul. 11, 1996 (now U.S. Pat. No. 6,235,290) (WO 98/02546), assigned to University of Manitoba and the disclosure of which is incorporated herein by reference, describes an immunogenic composition for in vivo administration to a host for the generation in the host of a protective Immune response to a major outer membrane protein (MOMP) of a strain of *Chlamydia*, comprising a non-replicating vector comprising a nucleotide sequence encoding a MOMP or MOMP fragment that generates a MOMP specific immune response, and a promoter sequence operatively coupled to the nucleotide sequence for expression of the MOMP or MOMP fragment in the host; and a pharmaceutically-acceptable canter therefor.

Copending U.S. patent application Ser. No. 08/713,236 filed Sep. 16, 1996 (now U.S. Pat. No. 6,464,979) (WO 98/10789), assigned to Connaught Laboratories Limited and the disclosure of which is incorporated herein by reference, describes an immunogenic composition, comprising the major outer membrane protein (MOMP) of a strain of *Chlamydia*, which may be *Chlamydia trachomatis*, and an immunostimulating complex (ISCOM).

SUMMARY OF INVENTION

The present invention provides a novel immunization strategy to provide protection against disease caused by infection of members of the Chlamydiae family, particularly *Chlamydia trachomatis* and materials used therein. The immunization strategy provided herein leads to a stronger protective immune response than other strategies.

According to one aspect of the invention, there is provided a method of immunizing a host against disease caused by infection by *Chlamydia* which comprises:

initially administering to the host an immunoeffective amount of an attenuated bacteria harbouring a nucleic acid sequence encoding at least one immunoprotective-inducing *Chlamydia* protein or fragment thereof which generates a *Chlamydia* protein-specific immune response, operatively connected to a eukaryotic expression element, such as the cytomegalovirus promoter, and subsequently administering to the host an immunoeffective amount of at least one purified *Chlamydia* protein or fragment thereof which generates a *Chlamydia* protein specific immune response, of the same at least one *Chlamydia* protein or immunogenic fragment thereof as used in the initial administration, to achieve a *Chlamydia* specific protective immune response in the host.

The attenuated bacteria may be an attenuated strain of *Salmonella* or *Shigella* and the nucleic acid sequence may be the MOMP gene or fragments thereof from a strain of *Chlamydia*, including *Chlamydia trachomatis* and *Chlamydia pneumoniae*. The boosting protein can be the MOMP protein or immunogenic fragments thereof from a strain of *Chlamydia*, including *Chlamydia trachomatis* and *Chlamydia pneumoniae*.

The administration steps may be effected to mucosal surfaces, such as by intranasal administration or by an initial intranasal administration of DNA followed by intramuscular administration of *Chlamydia* protein.

The immune response which is achieved in the host by the method of the invention preferably includes the production of *Chlamydia*-specific protection against live *Chlamydia* challenge and enhanced immunogenicity with greater delayed-type hypersensitivity (DTH) responses and high $IgG_2$ and $IgG_1$ antibody responses than achieved in other immunization procedures.

In another aspect, the present invention includes an attenuated strain of a bacterium harbouring a nucleic acid molecule encoding at least one immunoprotection-inducing *Chlamydia* protein or a fragment thereof which generates a *Chlamydia* protein specific immune response. The bacterium preferably is a strain of *Salmonella*, such as a strain of *Salmonella typhimurium*. The invention extends to such attenuated strain of a bacterium when used as an immunogen and to the use of such attenuated strain in the manufacture of an immunogen for administration to a host.

The present invention, in a further aspect, provides a method of immunizing a host against infection caused by a strain of *Chlamydia*, which comprises:

administering to the host an immunoeffective amount of an attenuated bacteria harbouring a nucleic acid molecule encoding at least one immunoprotection-inducing *Chlamydia* protein or a fragment thereof which generates a *Chlamydia* protein specific immune response. Any of the embodiments described herein with respect to the priming administration in the prime-boost immunization protocol described herein applies to this aspect of the invention.

BRIEF DESCRIPTION OF DRAWINGS

FIG. 1, containing panels A, B, C, D, E and F, shows the protection results of administering the MOMP-DNA either intramuscularly (panels A, B and C) or intranasally (panels D, E and F).

GENERAL DESCRIPTION OF THE INVENTION

The present invention relates to methods of immunization comprising an initial administration of a nucleic acid sequence encoding at least one *Chlamydia* protein or immunogenic fragment thereof, operatively connected to a eukaryotic expression element, delivered by an attenuated *Salmonella* and a subsequent administration of at least one protein or fragment thereof of the same protein of the *Chlamydia*. The at least one protein may comprise a *Chlamydia* protein, such as MOMP and may be formulated into an ISCOM for administration to the host. The at least one protein may be produced recombinantly or isolated from a chlamydial preparation.

To illustrate the present invention, plasmid DNA was constructed containing the MOMP gene and MOMP gene fragments from the *C. trachomatis* mouse pneumonitis strain (MoPn), which is a natural murine pathogen, permitting experimentation to be effected in mice. Primary infection in the model induces strong protective immunity to reinfection. For human immunization, a human pathogen strain is used, such as serovar C of *C. trachomatis*.

Figure 5:
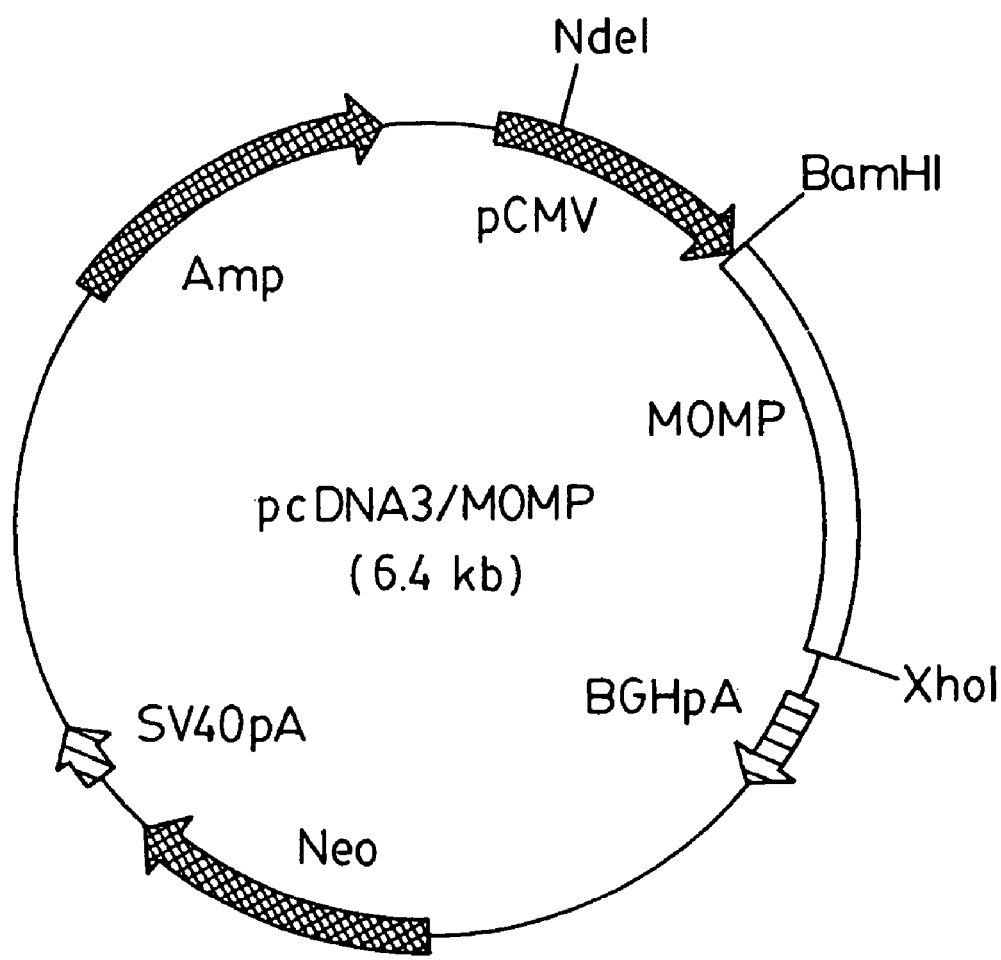
FIG. 5 shows the elements and construction of plasmid pcDNA3/MOMP, approximately 64 kb in size.

Any convenient plasmid vector may be used for the MOMP gene or fragment, such as pcDNA3, a eukaryotic expression vector (Invitrogen, San Diego, Calif., USA), containing a suitable promoter, such as a cytomegalovirus promoter. The MOMP gene or MOMP gene fragment may be inserted in the vector in any convenient manner. The gene or gene fragments may be amplified from *Chlamydia trachomatis* genomic DNA by PCR using suitable primers and the PCR product cloned into the vector. The MOMP gene-carrying plasmid may be transferred, such as by electroporation, into *E. coli* for replication therein. A MOMP-carrying plasmid, pcDNA3/MOMP, of approximately 64 kb in size, is shown in FIG. 5. Plasmids may be extracted from the *E. coli* in any convenient manner.

The plasmid containing the MOMP gene or MOMP gene fragment may be used to transform an attenuated *Salmonella* bacteria according to standard protocols, such as electroporation (ref. 43).

As described above, the primary (priming) immunization may be effected by administration of an attenuated bacterial vector, such as *Salmonella*, wherein the transfected DNA is not expressed in the bacterial vector. The expression of the primary DNA is effected when the bacterial vector has released the DNA into the appropriate host cells, such as macrophages or dendritic cells. After uptake of the bacterial vector by the host cells, the auxotrophic bacteria dies after a few rounds of division due to their inability to synthesize the essential nutrients, such as amino acids or nucleotides. The plasmid DNA then is released into the cytoplasm of the infected host cells and the encoded gene expressed in the host cell.

The boosting immunization may be a *Chlamydia* protein incorporated into a immunostimulatory complex (ISCOM) or a recombinantly produced *Chlamydia* protein. The *Chlamydia* protein can also be an isolated native *Chlamydia* protein, which is extracted from a *Chlamydia* extract.

It is clearly apparent to one skilled in the art, that the various embodiments of the present invention may have applications in the fields of vaccination and the treatment of *Chlamydia* infections. A further non-limiting discussion of such uses is further presented below.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended as descriptive and not for purposes of limitation.

Example 1

This Example illustrates the preparation of a plasmid vector containing the MOMP gene.

A pMOMP expression vector was made as described in the aforementioned U.S. patent application Ser. No. 08/893, 381, now U.S. Pat. No. 6,235,290) (WO 98/02546). Briefly, the MOMP gene was amplified from *Chlamydia trachomatis* mouse pneumonitis (MoPn) strain genomic DNA by polymerase chain reaction (PCR) with a 5' primer (GGGGATC-CGCCACCATGCTGCCTGTGGGGAATCCT) (SEQ ID NO:1) which includes a BamHI site, a ribosomal binding site, an initiation codon and the N-terminal sequence of the mature MOMP of MoPn and a 3' primer (GGGGCTC-GAGCTATTAACGGAACTGAGC) (SEQ ID NO:2) which includes the C-terminal sequence of the MoPn MOMP, XhoI site and a stop codon. The DNA sequence of the MOMP leader peptide gene sequence was excluded. After digestion with BamHI and XhoI, the PCR product was cloned into the pcDNA3 eukaryotic II-selectable expression vector (Invitrogen, San Diego) with transcription under control of the human cytomegalovirus major intermediate early enhancer region (CMV promoter). The MOMP gene-encoding plasmid was transferred by electroporation into *E. coil* DH5αF which was grown in LB broth containing 100 μg/ml of ampicillin. The plasmids was extracted by Wizard™ Plus Maxiprep DNA purification system (Promega, Madison). The sequence of the recombinant MOMP gene was verified by PCR direct sequence analysis, as described (ref. 44). Purified plasmid DNA was dissolved in saline at a concentration of 1 mg/ml. The DNA concentration was determined by DU-62 spectrophotometer (Beckman, Fullerton, Calif.) at 260 nm and the size of the plasmid was compared with DNA standards in ethidium bromide-stained agarose gel.

The MOMP gene containing plasmid, pcDNA3/MOMP, and its constitutive elements are shown in FIG. 5.

Example 2

This Example illustrates DNA immunization of mice.

A model of murine pneumonia induced by the *C. trachomatis* mouse pneumonitis strain (MoPn) was used (ref. 45). Unlike most strains of *C. trachomatis*, which are restricted to producing infection and disease in humans, MoPn is a natural murine pathogen. It has previously been demonstrated that primary infection in this model induces strong protective immunity to reinfection. In addition, clearance of infection is related to CD4 Th1 lymphocyte responses and is dependent on MHC class II antigen presentation (ref. 45).

Three different concentrations of MOMP-DNA were compared, administered either intramuscularly or intranasally (FIG. 1). The results clearly show that mucosal delivery of naked MOMP-DNA is protective and appeared more so than intramuscularly delivered MOMP-DNA. Intranasal delivery of MOMP-DNA was evaluated in multiple experiments to determine its reproducibility. As shown in Table 1, mucosal delivery of MOMP-DNA evoked protective immune responses but the magnitude of the protective index was highly variable, ranging from 0.5 to 4.1 $\log_{10}$ protection in different experiments. The basis for such variability may be due to the limited immunogenicity of naked DNA vaccination since challenging vaccinated animals with a higher inoculum of MoPn markedly reduced the protective index. Naked DNA applied to a mucosal surface may also have a very variable fate with some being degraded by extracellular nucleases and some being taken up the somatic cells.

Example 3

This Example illustrates the delivery of DNA with attenuated *Salmonella*.

*Salmonella typhimurium* strain 22-4 is described in ref. 46. Such strain was transfected with pcDNA3/MOMP and pcDNA3 by electroporation. Attenuated strains of *Salmonella*, transfected with plasmid DNA, were cultured for 16 to 25 hours at 37° C., without shaking in Luria Broth (LB) medium containing 100 μg/ml ampicillin. Bacteria were collected by centrifugation and resuspended in PBS. Different concentrations of *Salmonella* were diluted with PBS and the same volume of 10% sodium bicarbonate was added immediately before immunization. Groups of 5 to 10 female Balb/c mice, 6 to 8 weeks of age, were deprived of water for 5 to 6 hours before immunization. Approximately $10^5$ to $10^{10}$ CFU of bacteria in 100 μl were fed by feeding needles (Ejay International Inc.). Four inoculations at 2 week intervals were administered.

Figure 2A:
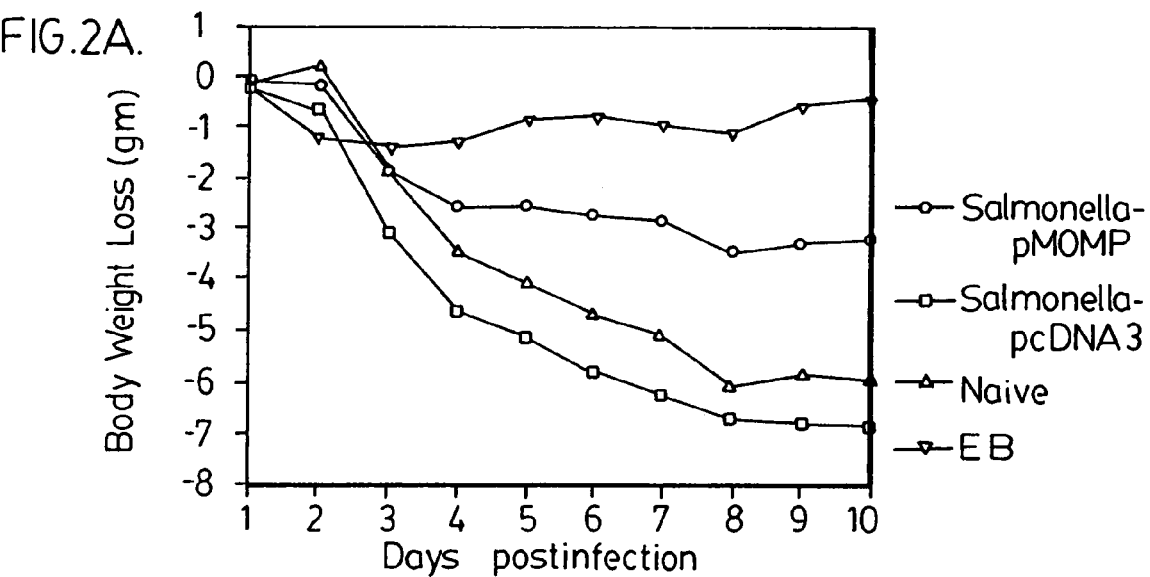
FIG. 2, containing panels A, B and C, shows the protection results from mice immunized with *Salmonella* transfected with MOMP-DNA (pcDNA3).
Figure 2B:
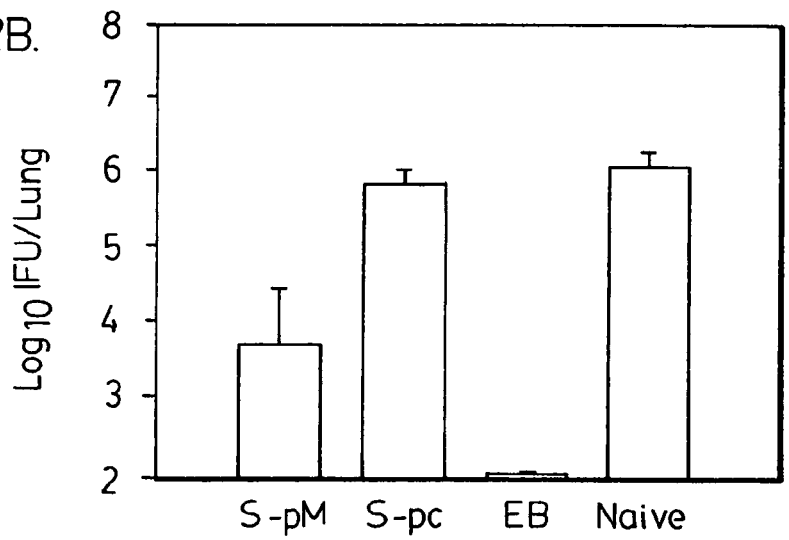
Figure 2C:
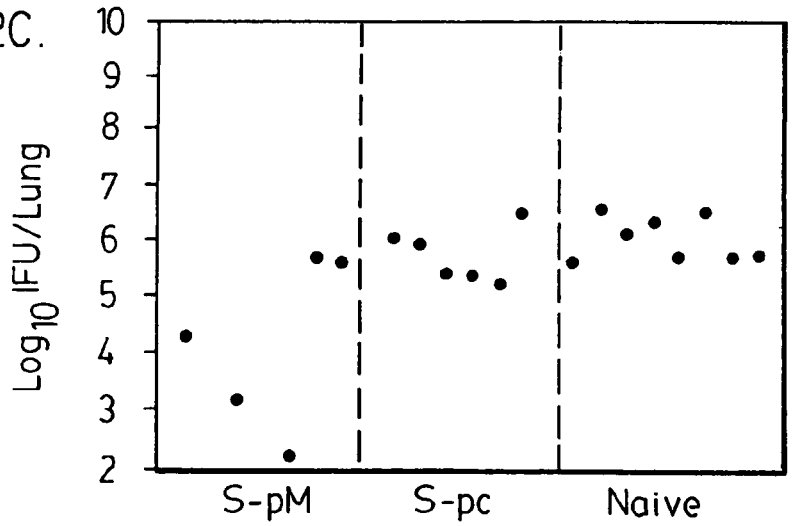

As shown in FIG. 2, mice immunized with *Salmonella* transfected with MOMP-DNA had partial protection against lung challenge with MoPn. Immunization at one mucosal surface (the gut) provides protection against challenge infection at a distant mucosal surface (the lung).

Example 4

This Example illustrates a DNA prime and protein boost immunization schedule in mice.

Figure 3A:
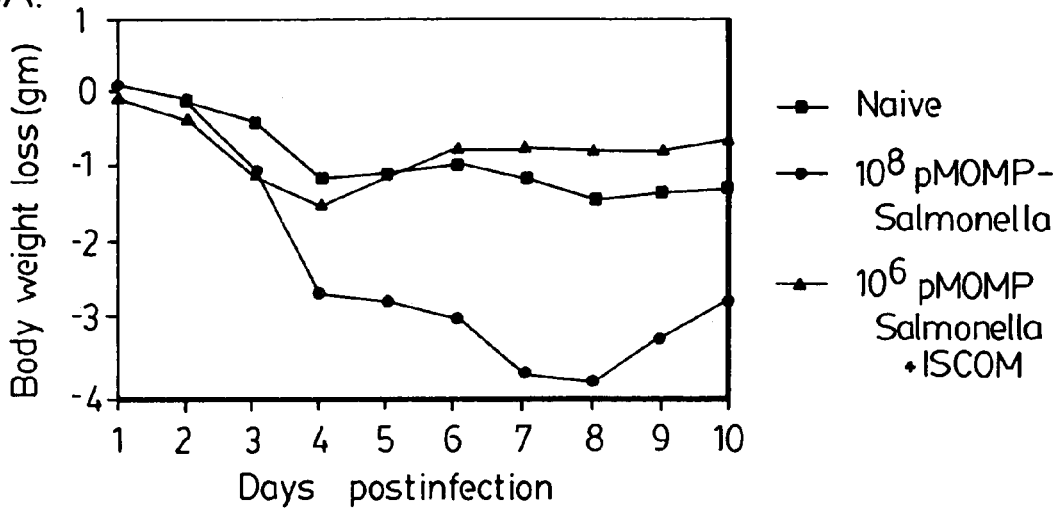
FIG. 3, containing panels A, B and C, shows the protection results from mice intranasally immunized with *Salmonella* transfected with pcDNA3, then boosted intramuscularly with MOMP embedded in ISCOM.
Figure 3B:
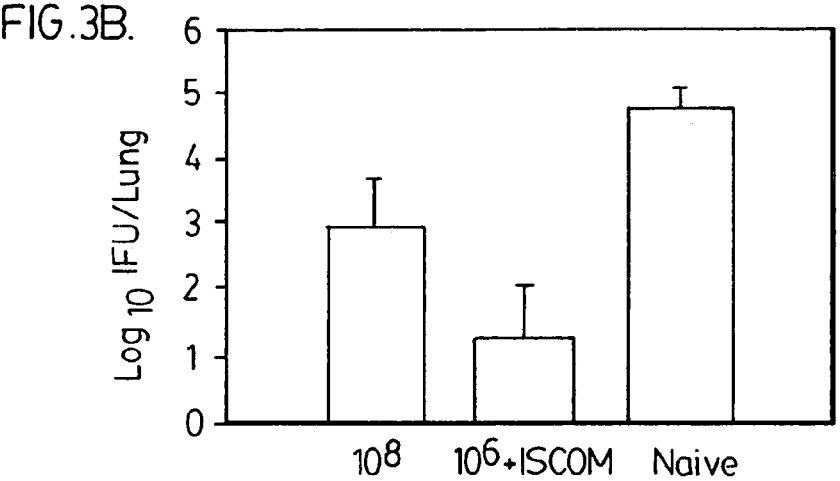
Figure 3C:
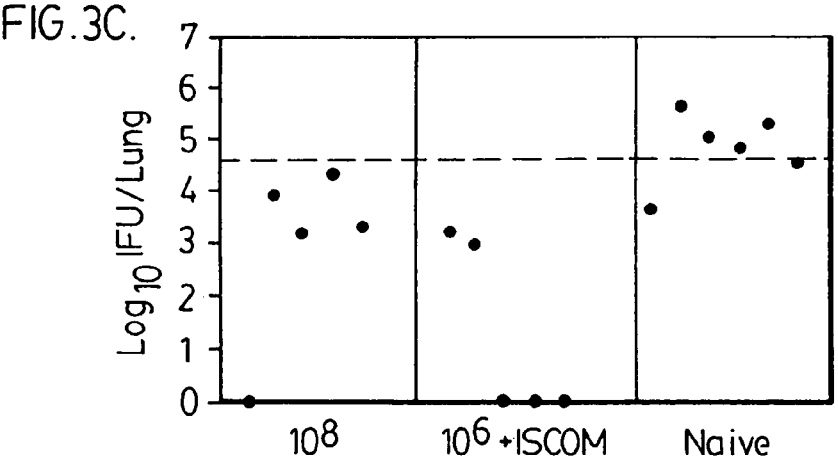
Figure 4A:
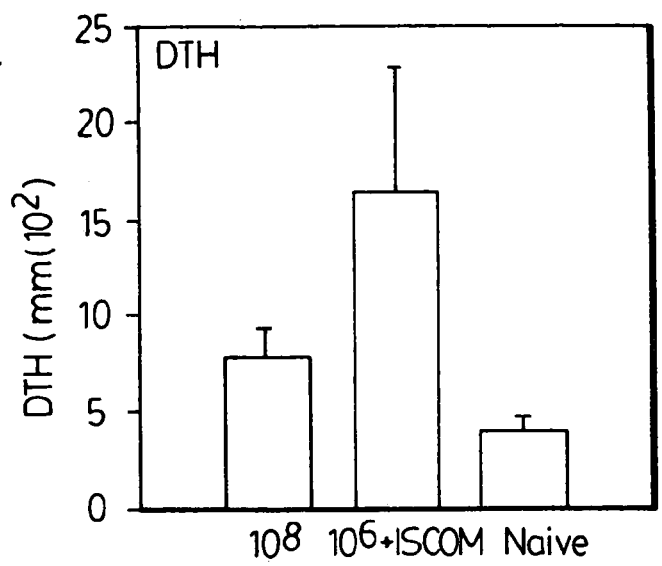
FIG. 4, containing panels A, B and C, shows the DTH response (panel A) and the $IgG_{2a}$ (panel B) and $IgG_1$ (panel C) antibody responses from mice primed intranasally with the *Salmonella* delivered DNA (pcDNA3) then boosted intramuscularly with the MOMP-ISCOM protein. The data represent means±SEM of $\log_{10}$ titres of the antibody. * represents p<0.05, when compared with naive group and group immunized with $10^8$ CFU pMOMP-*Salmonella* only.
Figure 4B:
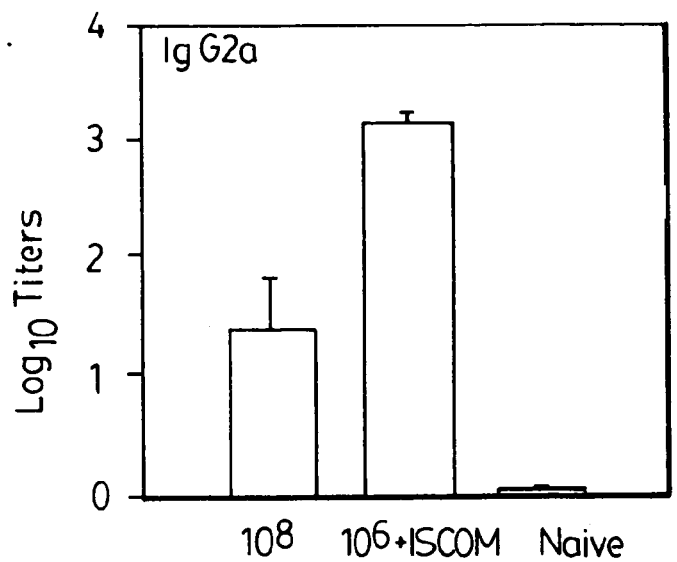
Figure 4C:
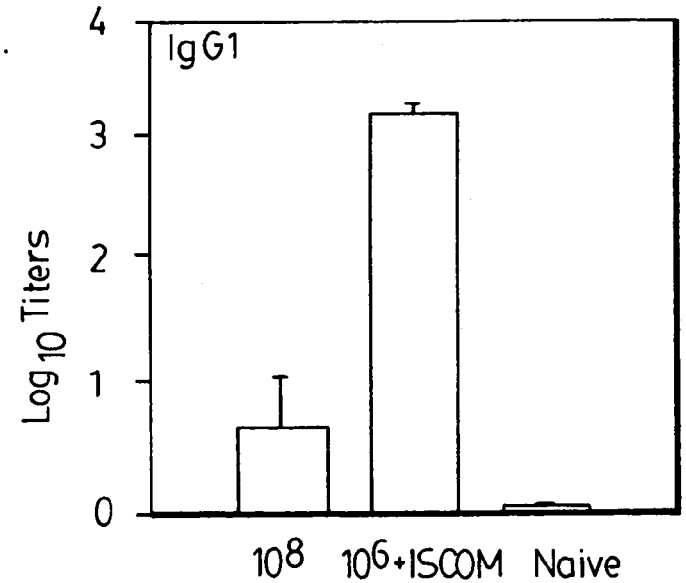

MOMP-DNA transfected *Salmonella*, prepared as described in Example 3, administered at $10^8$ cfu was compared to MOMP-DNA transfected *Salmonella* administered at $10^6$ cfu among groups of Balb/c mice orally immunized at two-week intervals on four occasions. Mice immunized with $10^6$ cfu had a single protein boost intramuscularly with 1 μg MoPn MOMP embedded in ISCOM (14) at the time of the fourth immunization. The ISCOM preparation was prepared as described in aforementioned U.S. patent application Ser. No. 08/718,236 (WO098/10789). The mice were challenged with 5000 IFU MoPn EB intranasally two weeks after the last immunization. Challenged mice were sacrificed at day 10 postinfection. The body weight was measured daily after infection until mice were sacrificed (FIG. 3, panel A). These mice were much better protected than mice given $10^8$ cfu *Salmonella* without a protein boost, as described in Example 3. *Chlamydia* EB growth in the lungs at day 10 postinfection was analyzed by quantitative tissue culture (FIG. 3, panel B and C). In. FIG. 3, panel B, the data represents the mean±SEM of $\log_{10}$ IFU per lung of 5 to 6 mice and panel C represents the results observed in individual mice. DNA primed, protein boosted mice also demonstrated enhanced immunogenicity with greater DTH responses (FIG. 4, panel A) and higher serum $IgG_2$ and $IgG_1$ antibody responses (FIG. 4, panels B and C). Sera were collected from immunized mice 2 weeks after the last immunization. MoPn-specific $IgG_{2a}$ (panel B) and $IgG_1$ (panel C) antibodies were tested by ELISA.

Example 5

This Example describes the measurement of MoPn-specific delayed-type hypersensitivity (DTH).

To evaluate DTH, 25 μl of ultraviolet (UV)-killed MoPn EBs ($2\times10^5$ IFU) in SPG buffer 25 was injected into the right hind footpad of mice and the same volume of SPG buffer was injected into the left hind footpad as a control. Footpad swelling was measured at 48 hours and 72 hours post injection using a dila-gauge caliper. The difference between the thickness of the two footpads was used as a measure of the DTH response.

SUMMARY OF DISCLOSURE

In summary of this disclosure, the present invention provides methods of immunizing a host against *Chlamydia* infection using DNA carried by an attenuated bacteria and materials used in such procedures. Modifications are possible within the scope of the invention.

TABLE 1

Intranasal (IN) immunization with MOMP-DNA evokes protective immunity to *Chlamydia trachomatis* MoPn lung infection.

| EXPERIMENT | LOG10 IFU/LUNG | | PROTECTIVE | CHALLENGE |
|---|---|---|---|---|
| Number | PcDNA3-IN | pMOMP-IN | Index | Inoculum (IFU) |
| 2 | 4.93 ± 0.68 (N = 7) | 3.65 ± 0.94 (N = 6) | 1.28 | 1000 |
| 3 | 6.1 ± 0.32 (N = 4) | 3.0 ± 1.15 (N = 4) | 4.1 | 5000 |
| 4 | 4.4 ± 0.32 (N = 7) | 3.9 ± 0.13 (N = 7) | 0.5 | 5000 × 2 |
| 7 | 5.39 ± 0.3 (N = 8) | 3.8 ± 0.63 (N = 8) | 1.59 | 5000 |

REFERENCES

1. Grayston, J. T. and S.-P. Wang. 1975. New knowledge of chlamydiae and the diseases they cause. J. Infect. Dis., 132: 87–104.
2. Grayston, J. T., S.-P. Wang, L.-J. Yeh, and C.-C. Kuo. 1985. Importance of reinfection in the pathogenesis of trachoma. Rev. Infect. Dis. 7:717–
3. Taylor, H. R., et al., 1982. Animal Model of Trachema. II. The importance of repeated infection. Invest. Opthalmol. Visual. Sci. 23:507–515.
4. Taylor, H. R., et al. 1981. An Animal Model for Cicatrizing Trachoma. Invest. Opthalmol. Sci. 21:422–433.
5. Caldwell, HD., et al. 1987. Tear and serum antibody response to *chlamydia trachomatis* antigens during acute chlamydial conjunctivitis in monkeys as determined by immunoblotting. Infect. Immun. 55:93–98.
6. Wang, S.-P., et al., 1985. Immunotyping of *Chlamydia trachomatis* with monoclonal antibodies. J. Infect. Dis. 152:791–800.
7. Nichols, R. L., et al., 1973. Immunity to Chlamydial infections of the eye. VI. Homologous neutralization of trachoma infectivity for the owl monkey conjunctivae by eye secretions from humans with trachoma. J. Infect. Dis. 127:429–432.
8. Orenstein, N. S., et al., 1973. Immunity to chlamydial infections of the eye V. Passive transfer of antitrachoma antibodies to owl monkeys. Infect. Immun. 7:600–603.
9. Ramsey, K H, et al., (March. 1991) Resolution of *Chlamydia* Genital Infection with Antigen-Specific T-Lymphocyte Lines. Infect. and Immun. 59:925–931.
10. Magee, D M, et al., (1995). Role of CD8 T Cells in Primary *Chlamydia* Infection. Infect. Immun. February 1995. 63:516–521.
11. Su, H. and Caldwell, H D., (1995) CD4+ T Cells Play a Significant Role in Adoptive Immunity to *Chlamydia trachomatis* Infection of the Mouse Genital Tract. Infect. Immun. September 1995, 63:3302–3308.
12. Beatty, P R., and Stephens R S., (1994) CD8+ T Lymphocyte-Mediated Lysis of *Chlamydia*-Infected L Cells Using an Endogenous Antigen Pathway., Journal of Immun. 1994, 153:4588.
13. Starnbach, M N., Bevan, M J. and Lampe, M F. (1994), Protective Cytotoxic T. Lymphocytes are Induced During Murine Infection with *Chlamydia trachomatis*, Journal of Immun. 1994, 153:5183.
14. Stambach, M N, Bevan, M J. And Lampe, M F., (1995), Murine Cytotoxic T. Lymphocytes Induced Following *Chlamydia trachomatis* Intraperitonal or Genital Tract Infection Respond to Cells Infected with Multiple Serovars., Infect. & Immun. Sept. 1995, 63:3527–3530.
15. Igietseme, J U, (1996), Molecular mechanism of T-cell control of *Chlamydia* in mice: role of nitric oxide in vivo. Immunology 1996, 88:1–5.
16. Igietseme. J U, (1996), The Molecular mechanism of T-cell control of *Chlamydia* in mice; role of nitric oxide. Immunology 1996, 87:1–8.
17. Ward, M. E. 1992. Chlamydial vaccines—future trends. J. Infection 25, Supp. 1:11–26.
18. Caldwell, H. D., et al., (1981). Purification and partial characterization of the major outer membrane protein of *Chlamydia trachomatis*. Infect. Immun. 31:1161–1176.
19. Bavoil, P., Ohlin, A. and Schachter, J., (1984) Role of Disulfide Bonding in Outer Membrane Structure and Permeability in *Chlamydia trachomatis*. Infect. Immun., 44: 479–485.
20. Campos, M., et al., (1995) A *Chlamydia* Major Outer Membrane Protein Extract as a *Trachoma* Vaccine Candidate., Invest. Opthalmol. Vis. Sci. 36:1477–1491.
21. Zhang Y.-X., et al., (1989). Protective monoclonal antibodies to *Chlamydia trachomatis* serovar- and serogroup-specific major outer membrane protein determinants. Infect. Immun. 57:636–638.
22. Zhang, Y.-X., et al., 1987. Protective monoclonal antibodies recognise epitopes located on the major outer membrane protein of *Chlamydia trachomatis*. J. Immunol. 138:575–581.
23. Department of Health and Human Services, (1989) Nucleotide and amino acid sequences of the four variable domains of the major outer membrane proteins of *Chlamydia trachomatis*. Report Nos: PAT-APPL-7-324664. National Technical Information Services, Springfield, Va.
24. Yuan, Y., et al. (1989) Nucleotide and deduced amino acid sequences for the four variable domains of the major outer membrane proteins of the 15 *Chlamydia trachomatis* serovars. Infect. Immun. 57:104–1049.
25. Su, H. and Caldwell, H. D. 1992. Immunogenicity of a chimeric peptide corresponding to T-helper and B-cell epitopes of the *Chlamydia trachomatis* major outer membrane protein. J. Exp. Med. 175:227–235.
26. Su. H., N. G. Watkins. Y.-X. Zhang and H. D. Caldwell (1990). *Chlamydia trachomatis*-host cell interactions: role of the chlamydial major outer membrane protein as an adhesin. Infect. Immun. 58:1017–1025.
27. Peeling, R., I. W. McClean and R. C. Brunham. (1984). In vitro neutralization of *Chlamydia trachomatis* with monoclonal antibody to an epitope on the major outer membrane protein. Infect. Immun. 46:484–488.
28. Lucero, M. E. and C.-C. Kuo. (1985). Neutralization of *Chlamydia trachomatis* cell culture infection by serovar specific monoclonal antibodies. Infect. Immun. 50:595–597.
29. Baehr. W., et al. (1988) Mapping antigenic domains expressed by *Chlamydia trachomatis* major outer membrane protein genes. Proc. Natl. Acad. Sci. USA, 85:4000–4004.
30. Stephens, R. S., et al. (1988) High-resolution mapping of serovar-specific and common antigenic determinants of the major outer membrane protein of *Chlamydia trachomatis*. J. Exp. Med. 167:817–831.
31. Conlan, J. W., I. N. Clarke and M. E. Ward. (1988). Epitope mapping with solid-phase peptides: Identification of type-, subspecies-, species-, and genus-reactive antibody binding domains on the major outer membrane protein of *Chlamydia trachomatis*. Mol. Microbiol. 2:673–679.
32. Conlan, J. W., et al., (1990). Isolation of recombinant fragments of the major outer membrane protein of *Chlamydia trachomatis*: their potential as subunit vaccines. J. Gen. Microbial. 136: 2013–2020.
33. Morrison, R. P., D. S. Manning, and H. D. Caldwell. (1992). Immunology of *Chlamydia trachomatis* infections. p. 57–84 In T. C. Quinn (ed) Sexually transmitted diseases. Raven Press Ltd., NY.
34. Kersten, G. F. A. and Crommelin, D. J. A. (1995). Liposomes and ISCOMs as vaccine formulations. Biochimica et Biophysica Acta 1241 (1995) 117–138.
35. Morein, B., et al., (1990) The iscom—a modern approach to vaccines seminars in Virology, Vol. 1, 1990: pp. 49–55.
36. Mowat & Reid, 1992. Preparation of Immune Stimulating Complexes (ISCOMs) as Adjuvants. Current Protocols in Immunology 1992. Supplement 4: 2.11.1. to 2.11.12.
37. M. A. Liu et al. 1995. Ann. N.Y. Acad. Sci. 772.
38. W. M. McDonnell and F. K. Askari 1996. N.Engl. J. Med. 334:42.
39. J. B. Ulmer et al. 1993. Science 259:1745.
40. M. Sedegah et al. 1994. Proc. Natl. Acad. Sci. U.S.A. 91:9866.
41. A. Darji et al. 1997. Cell 91:765–775.
42. D. R. Sizemore, 1997. Vaccine 15:804–807.
43. D. O'Callaghan and A. Charbit. 1990. Mol. Gen. Genet. 223:156–158.
44. R. Brunham et al. 1994. J. Clin. Invest. 94:458–463.
45. R. P. Morrison et al. 1995. Infect. Immun. 63:4661.
46. K. Y. Leung et al., 1991, PNAS 88(24):1147-4.

We claim:

1. A method of immunizing a host, which comprises:
administering to the host an attenuated auxotrophic bacteria harbouring a vector comprising a nucleic acid molecule encoding at least one immunoprotection-inducing *Chlamydia* protein or a fragment thereof which generates a *Chlamydia* protein specific immune response and a promoter operatively coupled to said nucleic acid nucleic acid molecule for expression of said *Chlamydia* protein or fragment thereof by cells of the host but not by said attenuated auxotrophic bacteria.

2. The method of claim 1 wherein said immunoprotection inducing *Chlamydia* protein or fragment thereof is a major outer membrane protein (MOMP) of a strain of *Chlamydia*.

3. The method of claim 2 wherein said strain of *Chlamydia* is a strain of *Chlamydia pneumoniae*.

4. The method of claim 2 wherein said strain of *Chlamydia* is a strain of *Chlamydia trachomatis*.

5. The method of claim 1 wherein said promoter is a cytomegalovirus promoter.

6. The method of claim 1 wherein said vector is a plasmid vector.

7. The method of claim 6 wherein said plasmid vector is pcDNA3/MOMP as seen in FIG. 5.

8. The method of claim 5 wherein said attenuated bacteria is an attenuated strain of *Salmonella*.

9. The method of claim 8 wherein said attenuated strain of *Salmonella* is an attenuated strain of *Salmonella typhimurium*.

10. The method of claim 1 wherein said administration is effected to mucosal surfaces.

11. The method of claim 10 wherein said administration is effected by intranasal administration.

* * * * *